United States Patent [19]

Hilboll et al.

[11] Patent Number: 4,699,914

[45] Date of Patent: Oct. 13, 1987

[54] IMIDAZOLE GROUP CONTAINING 2(1H)-PYRIDONES AND METHOD FOR TREATING HEART INSUFFICIENCIES IN HUMANS

[75] Inventors: Gerd Hilboll, Pulheim; Ille-Stephanie Doppelfeld, Bergheim-Glessen; Gerrit Prop, Pulheim, all of Fed. Rep. of Germany

[73] Assignee: A. Nattermann & Cie GmbH, Cologne, Fed. Rep. of Germany

[21] Appl. No.: 771,984

[22] Filed: Sep. 3, 1985

[30] Foreign Application Priority Data

Sep. 15, 1984 [DE] Fed. Rep. of Germany ....... 3433953

[51] Int. Cl.⁴ .................. C07D 409/14; A61K 31/415
[52] U.S. Cl. ...................................... 514/341; 546/278
[58] Field of Search .......................... 546/278; 514/341

[56] References Cited

U.S. PATENT DOCUMENTS 4,503,061 3/1985 Bristol et al. ....................... 546/278

FOREIGN PATENT DOCUMENTS 0102227 3/1984 European Pat. Off. .
0109628 5/1984 European Pat. Off. .

Primary Examiner—Jane T. Fan
Attorney, Agent, or Firm—Pearne, Gordon, McCoy & Granger

[57] ABSTRACT

The present invention is directed to new, an imidazole group containing 2(1H)-pyridones of formula I

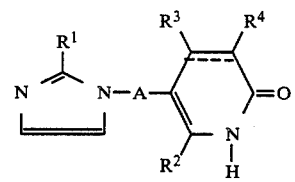

salts thereof and process for treating congestive heart failure in humans.

8 Claims, No Drawings

IMIDAZOLE GROUP CONTAINING 2(1H)-PYRIDONES AND METHOD FOR TREATING HEART INSUFFICIENCIES IN HUMANS

FIELD OF THE INVENTION

Subject-matter of the present invention are new 2(1H)-pyridones substituted in the 5-position by an imidazolylthienyl or imidazolylphenyl group and 3,4-dihydro-derivatives thereof as well as the acid addition salts thereof with pharmacologically acceptable acids and processes for the treatment of human beings suffering from congestive heart failure by administering such compounds.

DISCUSSION OF THE PRIOR ART

In European patent No. 109628, there are described 2(1H)-pyridones and their 3,4-dihydro-derivatives substituted in the 5-position by hydroxyphenyl, methoxyphenyl or pyridyl groups as well as their use as cardiotonic agents.

In European patent application No. 102227, there are described among others positively ionotropic-acting 5-(imidazolyl-phenyl)-2(1H)-pyridones which can be substituted in the 3-position by H, CH$_2$OH, F, Cl, Br, CN, COOR, CONR'R" and NR'R".

SUMMARY OF THE INVENTION

The present invention is directed to 2(1H)-pyridones of formula I

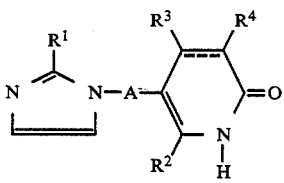

wherein
  ==== is a single bond between two carbon atoms,
  R$^1$, R$^3$ and R$^4$ independent from each other are hydrogen or a methyl group,
  R$^2$ is a C$_{1-4}$ lower alkyl group and
  A represents the phenylene and thienylene groups, in particular the 1,4-phenylene group of formula

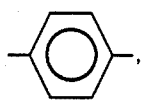

the 2,4-thienylene group of formula

or the 2,5-thienylene group of formula

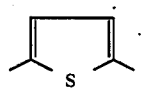

The present invention is further directed to 2(1H)-pyridones of formula I wherein
  ==== is a double bond between two carbon atoms,
  R$^1$ and R$^3$ independent from each other are hydrogen or a methyl group,
  R$^2$ is a C$_{1-4}$ lower alkyl group,
  R$^4$ is a methyl group and
  A represents the 1,4-phenylene group.

The invention is further directed to 2(1H)-pyridones of formula I wherein
  ==== is a double bond between two carbon atoms,
  R$^1$ and R$^3$ independent from each other are hydrogen or a methyl group,
  R$^2$ is a C$_{1-4}$-lower alkyl group and
  R$^4$ is hydrogen, methyl, —COOH, —CN, —CONH$_2$ or —NH$_2$ and
  A is the 2,4-thienylene group of formula

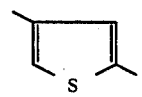

or the 2,5-thienylene group of formula

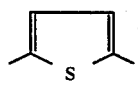

Those compounds of formula I where ==== is a single bond (3,4-dihydro-2(1H)-pyridones) have a chirality center at the positions 3 and 4, respectively, of the pyridine nucleus, if the substituents R$^3$ and/or R$^4$ are not hydrogen and thus they can be present as racemates or in the form of enantiomers. If a separation of the racemates is desired, it is accomplished according to processes known per se with an optically active acid such as dibenzoyl tartaric acid or campher-10-sulfonic acid through the formation of diastereomeric salts or by chromatography at an optically active column material.

The invention also comprises the pharmaceutically usable acid addition salts of compounds of formula I, i.e. the acid addition salts with pharmacologically acceptable acids, such as those with hydrochloric acid, hydrobromic acid, sulfuric acid or phosphoric acid or with organic acids such as acetic acid, propionic acid, oxalic acid, malonic acid, glycolic acid, succinic acid, maleic acid, fumaric acid, malic acid, citric acid, tartaric acid, lactic acid, benzoic acid.

Examples of compounds of the present invention are the following:
3,4-dihydro-5-[4-(1-imidazolyl)-phenyl]-6-methyl-2(1H-pyridone
3,4-dihydro-5 -[5-(1-imidazolyl)-2-thienyl]-6-methyl--2(1H)-pyridone
3,4-dihydro-5-[4-(1-imidazolyl)-2-thienyl]-6-methyl-2(1H)-pyridone
3,4-dihydro-5-[4-(2-methyl-1-imidazolyl)-phenyl]-6-methyl-2 (1H)-pyridone
3,4-dihydro-3,6-dimethyl-5-[4-(1-imidazolyl)-phenyl]-2 (1H)-pyridone
3,4-dihydro-3,6-dimethyl-5-[4-(1-imidazolyl)-2-thienyl]-2 (1H)-pyridone
3,4-dihydro-3,6-dimethyl-5-[5-(1-imidazolyl)-2-thienyl]-2(1H)-pyridone
3,4-dihydro-3,6-dimethyl-5-[4-(2-methyl-1-imidazolylphenyl]-2(1H)-pyridone 3,4-dihydro-4,6-dimethyl-5-[4-(1-imidazolyl)-phenyl]-2(1H)-pyridone
3,4-dihydro-4,6-dimethyl-5-[5-(1-imidazolyl)-2-thienyl]-2 (1H)-pyridone
3,4-dihydro-4,6-dimethyl-5-[4-(1-imidazolyl)-2-thienyl]-2 (1H)-pyridone
3,4-dihydro-4,6-dimethyl-5-[4-(2-methyl-1-imidazolyl)-phenyl]-2-(1H)-pyridone
3,4-dihydro-5-[4-(1-imidazolyl)-phenyl]-3-methyl-6-propyl-2 (1H)-pyridone
6-butyl-3,4-dihydro-5-[4-(1-imidazolyl)-phenyl]-3-methyl-2 (1H)-pyridone
3,4-dihydro-6-ethyl-5-[4-(1-imidazolyl)-phenyl]-3-methyl-2 (1H)-pyridone
3,4-dihydro-6-ethyl-5-[4-(1-imidazolyl)-phenyl]-2(1H)-pyridone
3,4-dihydro-6-ethyl-5-[4-(2-methyl-1-imidazolyl)-phenyl]-2 (1H)-pyridone
3,4-dihydro-6-ethyl-5-[4-(2-methyl-1-imidazolyl)-phenyl]-3-methyl-2(1H)-pyridone
3,4-dihydro-6-ethyl-5-[5-(1-imidazolyl)-2-thienyl]-2(1H)-pyridone
3,4-dihydro-6-ethyl-5-[5-(1-imidazolyl)-2-thienyl]-3-methyl-2(1H)-pyridone
3,4-dihydro-6-ethyl-5-[4-(1-imidazolyl)-2-thienyl]-2(1H)-pyridone
3,4-dihydro-6-ethyl-5-[4-(1-imidazolyl)-2-thienyl]-3-methyl-2(1H)-pyridone
5-[5-(1-imidazolyl)-2-thienyl]-6-methyl-2(1H)-pyridone
5-[4-(1-imidazolyl)-2-thienyl]-6-methyl-2(1H)-pyridone
3,6-dimethyl-5-[4-(1-imidazolyl)-phenyl]-2(1H)-pyridone
3,6-dimethyl-5-[5-(1-imidazolyl)-2-thienyl]-2(1H)-pyridone
3,6-dimethyl-5-[4-(1-imidazolyl)-2-thienyl]-2(1H)-pyridone
3,6-dimethyl-5-[4-(2-methyl-1-imidazolyl)-phenyl]-2-(1H)-pyridone
4,6-dimethyl-5-[5-(1-imidazolyl)-2-thienyl]-2(1H)-pyridone
4,6-dimethyl-5-[4-(1-imidazolyl)-2-thienyl]-2(1H)-pyridone
6-ethyl-5-[4-(1-imidazolyl)-phenyl]-3-methyl-2(1H)-pyridone
5-[4-(1-imidazolyl)-phenyl]-3-methyl-6-propyl-2(1H)-pyridone
6-butyl-5-[4-(1-imidazolyl)-phenyl]-3-methyl-2(1H)-pyridone
6-ethyl-5-[5-(1-imidazolyl)-2-thienyl]-2(1H)-pyridone
6-ethyl-5-[4-(2-methyl-1-imidazolyl)-phenyl]-3-methyl-2 (1H)-pyridone
6-butyl-5-[4-(1-imidazolyl)-2-thienyl]-3-methyl-2(1H)-pyridone
6-butyl-5-[5-(1-imidazolyl)-2-thienyl]-3-methyl-2(1H)-pyridone
5-[4-(1-imidazolyl)-2-thienyl]-3-methyl-6-propyl-2(1H)-pyridone
5-[5-(1-imidazolyl)-2-thienyl]-3-methyl-6-propyl-2(1H)-pyridone
6-ethyl-5-[5-(1-imidazolyl)-2-thienyl]-3-methyl-2(1H)-pyridone
6-ethyl-5-[-(1-imidazolyl)-2-thienyl]-2(1H)-pyridone
6-ethyl-5-[4-(1-imidazolyl)-2-thienyl]-3-methyl-2(1H)-pyridone
1,2-dihydro-5-[5-(1-imidazolyl)-2-thienyl]-6-methyl-2-oxopyridin-3-carboxylic acid nitrile
1,2-dihydro-5-[4-(1-imidazolyl)-2-thienyl]-6-methyl-2-oxopyridin-3-carboxylic acid nitrile
1,2-dihydro-4,6-dimethyl-5-[4-(1-imidazolyl)-2-thienyl]-z-oxo-pyridin-3-carboxylic acid nitrile
1,2-dihydro-5-[5-(1-imidazolyl)-2-thienyl]-6-methyl-2-oxopyridin-3-carboxylic acid
1,2-dihydro-5-[4-(1-imidazolyl)-2-thienyl]-6-methyl-2-oxopyridin-3-carboxylic acid
1,2-dihydro-5-[5-(1-imidazolyl)-2-thienyl]-6-methyl-2-oxopyridin-3-carboxylic acid amide
1,2-dihydro-5-[4-(1-imidazolyl)-2-thienyl]-6-methyl-2-oxopyridin-3-carboxylic acid amide
3-amino-5-[5-(1-imidazolyl)-2-thienyl]-6-methyl-2(1H)-pyridone
3-amino-5-[4-(1-imidazolyl)-2-thienyl]-6-methyl-2(1H)-pyridone The preparation of the compounds of the present invention is accomplished by using known processes or processes analoguous to them. Thus, the 3,4-dihydro-2(1H)-pyridones of the formula I, wherein $====$ is a single bond between two carbon atoms, $R^1$, $R^3$ and $R^4$ independent from each other are hydrogen or a methyl radical and $R^2$ is a $C_{1-4}$-lower alkyl group and wherein A represents

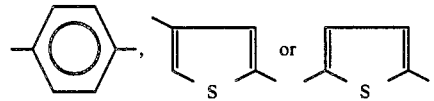

are formed by reacting an alkanone of the formula IV

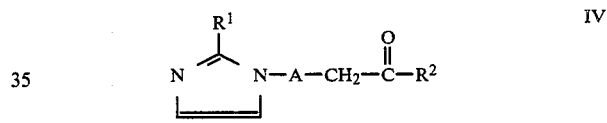

wherein A is phenylene or thienylene and $R^2$ is a $C_{1-4}$-lower alkyl radical with an acrylic acid amide of the formula V

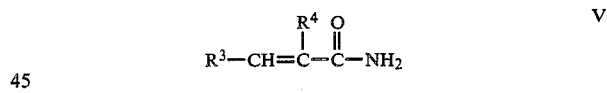

wherein $R^3$ and $R^4$ are hydrogen or a methyl radical.

The reaction is carried out at room temperature in an inert solvent such as 1,4-dioxane, dimethylformamide, tetrahydrofurane, N-methyl-pyrrolidone, dimethylsulfoxide, sulfolane, methanol, ethanol in the presence of a strong base, such as potassium tert-butoxide, sodium hydride, sodium methoxide, sodium ethoxide, sodium amide, preferably in 1,4-dioxane with potassium tert-butoxide as base. If necessary, the reaction mixtures can be heated to temperatures up to about 100° C. for a short time to effect the condensation of 5-oxo-pentanoic acid amide of the formula VIII, which are formed transitorily by Michael-addition and which also can be isolated

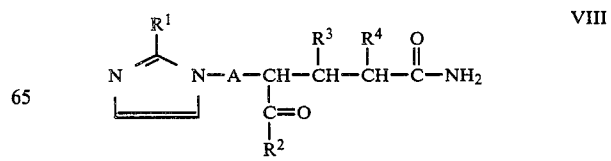

wherein $R^1$, $R^2$, $R^3$, $R^4$ and A have the meanings as defined above. The alkanones used as starting compounds of the formula IV can be prepared for example according to or analoguously to EP No. 102 227.

Suitable starting compounds of the formula IV are for example:
1-[4-(1-imidazolyl)-phenyl]-2-propanone
1-[4-(1-imidazolyl)-phenyl]-2-butanone
1-[4-(1-imidazolyl)-phenyl]-2-pentanone
1-[4-(1-imidazolyl)-phenyl]-2-hexanone
1-[4-(2-methyl-1-imidazolyl)-phenyl]-2-propanone
1-[4-(2-methyl-1-imidazolyl)-phenyl]-2-butanone
1-[4-(2-methyl-1-imidazolyl)-phenyl]-2-pentanone
1-[4-(2-methyl-1-imidazolyl)-phenyl]-2-hexanone
1-[5-(1-imidazolyl)-2-thienyl]-2-propanone
1-[5-(1-imidazolyl)-2-thienyl]-2-butanone
1-[5-(1-imidazolyl)-2-thienyl]-2-pentanone
1-[5-(1-imidazolyl)-2-thienyl]-2-hexanone
1-[4-(1-imidazolyl)-2-thienyl]-2-propanone
1-[4-(1-imidazolyl)-2-thienyl]-2-butanone
1-[4-(1-imidazolyl)-2-thienyl]-2-pentanone
1-[4-(1-imidazolyl)-2-thienyl]-2-hexanone
1-[5-(2-methyl-1-imidazolyl)-2-thienyl]-2-propanone As acrylic acid amides of the formula V for example the following compounds can be used: Acrylic acid amide, crotonic acid amide, methacrylic acid amide, tiglic acid amide.

Alternatively, the 3,4-dihydro-2(1H)-pyridones of the formula I can be prepared by using the Michael-reaction from alkanones of the formula IV and the acrylic acid nitriles of the formula IX

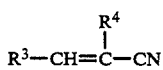

IX wherein $R^3$ and $R^4$ are hydrogen or a methyl group and subsequent treatment of the formed 5-oxo-pentanoic acid nitriles of the formula II

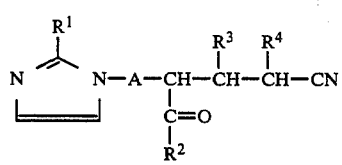

II wherein A, $R^1$, $R^2$, $R^3$, $R^4$ have the meanings as defined above, with strong acids. Thus, the reaction between the alkanones and the acrylic acid nitriles is carried out at temperatures between 0° and 100° C. in the presence of a strong base such as sodium hydride, sodium ethoxide, sodium methoxide, potassium tert-butoxide, sodium amide, preferably sodium methoxide, in an organic solvent such as methanol, ethanol, 1,4-dioxane, tetrahydrofurane, dimethylformamide, N-methylprrolidone, dimethylsulfoxide, preferable in methanol. The conversion of the 5-oxo-pentanoic acid nitriles of the formula II into the 3,4-dihydro-2(1H)-pyridones of the formula I is accomplished by treating with strong mineral acids such as concentrated sulfuric acid, hydrochloric acid, polyphosphoric acid, optionally in a suitable solvent such as acetic acid, ethanol, preferably by treatment with sulfuric acid in acetic acid at temperatures between 0° and about 100° C. Usable compounds of the formula IX are : acrylic acid nitrile, crotonic acid nitrile, methacrylic acid nitrile, tiglic acid nitrile.

A third possibility to prepare the 3,4-dihydro-2(1H)-pyridones of the formula I is the reaction of the alkanones of the formula IV with acrylic acid esters of the formula X

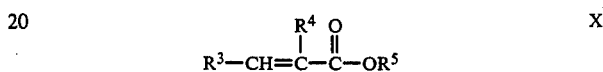

X wherein $R^3$, $R^4$ are hydrogen or a methyl group and $R^5$ is a $C_{1-4}$-lower alkyl radical, and subsequent reaction of the formed 5-oxo-pentanoic acid esters of the formula III

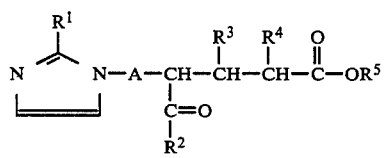

III wherein A, $R^1$, $R^2$, $R^3$, $R^4$, $R^5$ have the meanings as defined above, with ammonia or a suitable ammonium salt. The reaction of the alkanones of the formula IV with the acrylic acid esters of the formula X is carried out at temperatures between 0° and 100° C., optionally in a suitable organic solvent such as methanol, ethanol, dimethylformamide, dimethylsulfoxide in the presence of benzyl trimethyl ammonium hydrochloride or of another suitable catalyst. The further reaction of the compounds of the formula III with ammonia or a suitable ammonium salt such as ammonium acetate, ammonium chloride, ammonium carbonate, ammonium formate, is carried out at temperatures from 0° to 100° C. in a suitable solvent such as ethanol, methanol, 1,4-dioxane, dimethylformamide, dimethylsulfoxide, preferably it is carried out with ammonia under pressure.

As starting compounds of the formula X for example the following compounds can be used:
Acrylic acid methyl ester, acrylic acid ethyl ester, acrylic acid propyl ester, acrylic acid butyl ester, crotonic acid methyl ester, crotonic acid ethyl ester, methacrylic acid methyl ester, methacrylic acid ethylester, tiglic acid methyl ester, tiglic acid ethyl ester.

The processes for the preparation of the 3,4-dihydro-2(1H)-pyridones of the formula I can be illustrated by the following formula schemata :

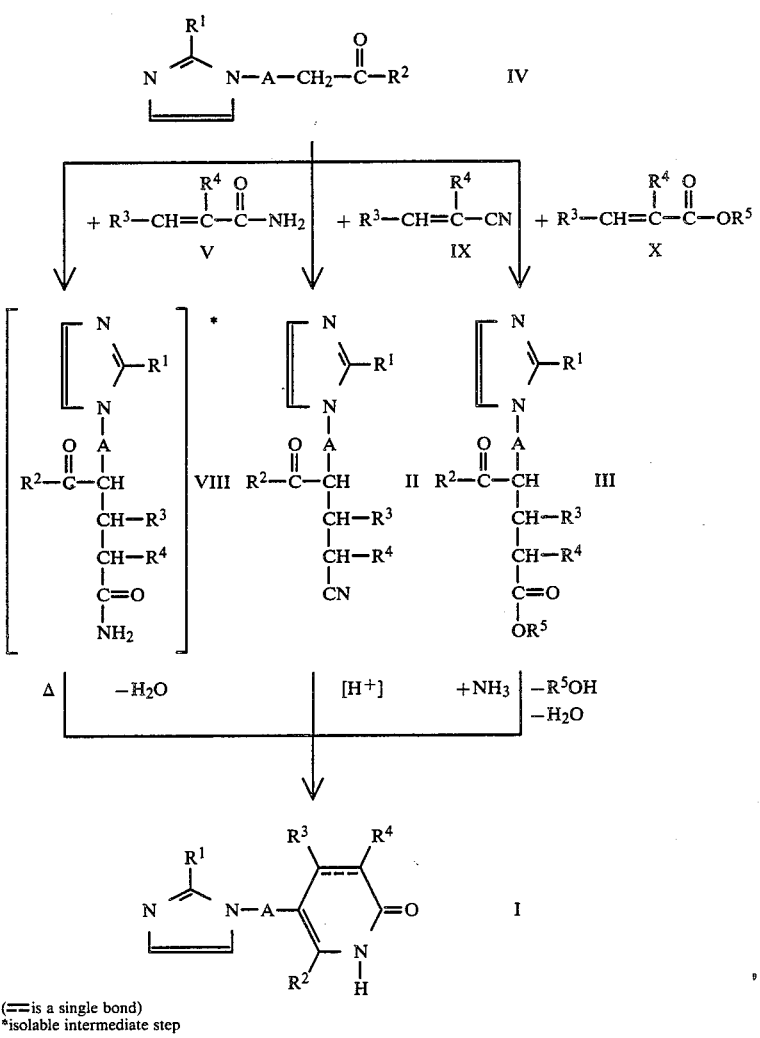

(═ is a single bond)
*isolable intermediate step

The preparation of the 2(1H)-pyridones of the formula I (═ is a double bond) wherein $R^4$ is hydrogen, methyl is accomplished analoguously to known processes by conversion of the corresponding 3,4-dihydro-2(1H)-pyridones of the formula I.

This conversion can be accomplished by dehydrogenation of the 3,4-dihydro-2(1H)-pyridones of the formula I in the presence of a noble metal catalyst with or without a support such as palladium in a high boiling organic solvent such as diethyleneglycol dimethylether, diethyleneglycol methyl-tert-butylether, diphenylether, at the reflux temperature.

A second conversion method is the heating of 3,4-dihydro-2(1H)-pyridones of the formula I with sulfur in a high boiling organic solvent such as diethylphthalate or a mixture of diphenyl and diphenylether to temperatures of 150°–250° C. The above mentioned conversion can also be carried out by treating the 3,4-dihydro-2(1H)-pyridones of the formula I with bromine in acetic acid at temperatures between 20° C. and the reflux temperature. It is preferred to convert the 3,4-dihydro-2(1H)-pyridones of the formula I into the corresponding 2(1H)-pyridones of the formula I by reaction with 3-nitrobenzene sulfonic acid in an alkaline-aqueous milieu at temperatures from 60° to 100° C.

The 2(1H)-pyridones of the formula I, (═ is a double bond) wherein $R^3=CH_3$, $R^4=H$, A=thienylene, can also be prepared by reaction of the alkanones of the formula IV (A=thienylene) with acetoacetamide in a mixture of polyphosphoric acid and methane sulfonic acid at temperatures from 70° to 150° C., preferably at 110° to 130° C.

The 2(1H)-pyridones of the formula I (═ is a double bond) wherein $R^4=CN$ are prepared analoguously to known processes.

Starting from the alkanones of the formula IV by reacting them with N,N-dimethylformamide dimethylacetal and N,N-dimethylacetamide dimethylacetal, respectively, of the formula VI

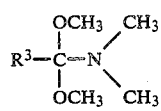

wherein $R^3$ is hydrogen or a methyl group, in a suitable solvent such as acetonitrile, the 2-(dimethylamino) ethenyl-alkanones of the formula VII are obtained

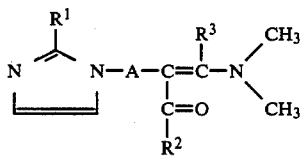

VII wherein $R^1$, $R^2$, $R^3$ and A have the meanings as defined above. These are reacted in a suitable solvent such as N,N-dimethylformamide in the presence of a strong base such as sodium hydride, sodium ethoxide, at temperatures from 50° to 150° C. with cyanoacetamide to form the 2(1H)-pyridones of the formula I, wherein $R^4$=CN.

These nitriles of the formula I can be further converted by using known processes, such as by hydrolysis in strong mineral acids like concentrated sulfuric acid, concentrated hydrochloric acid, into the corresponding carboxylic acid amides of the formula I or into carboxylic acids of the formula I, which in turn by decarboxylation in a suitable solvent such as diphenylether, at temperatures up to 250° C. can be converted thermically into the corresponding 2(1H)-pyridones of the formula I ( $\rightleftharpoons$ is a double bond) wherein $R^4$=hydrogen. Also the carboxylic acid amides and the carboxylic acids, respectively, of the formula I by using known decomposition processes such as Hoffmann decomposition Lossen decomposition Curtius decomposition can be converted into the corresponding amines of the formula I ( $\rightleftharpoons$ is a double bond, $R^4$=NH$_2$ ).

The advantageous use of the compounds of the formula I as cardiotonica is demonstrated by their activity in pharmacological standard tests such as the increase of the contractility of isolated guinea-pig arteria and or the increase of the heart contractility of anaesthetized cats or dogs accompanied with only little changes of the heart frequency and of the blood pressure.

The compounds of the present invention show a strong inhibition of the collagen-induced aggregation of human platelets in vitro besides the positive iontropic activity.

EVALUATION OF THE CARDIOTONIC ACTIVITY IN VIVO

Anaesthetized dog

The effects of increasing doses of the drugs were measured upon intravenous administration to anaesthetized dogs. As parameters myocardial contractility, heart rate and arterial blood pressure were registered.

Method

Adult mongrel dogs of either sex received a premedication of morphinhydrochloride (1.0 mg/kg s.c.). Thirty minutes later anaesthesia was induced by chloralose/urethane. The animals were heparinised with 500 I.U. heparin/kg (i.v.) as an initial dosage followed by doses of 250 I.U./kg given every 4 hours.

The trachea was intubated but the animals were allowed to breathe spontaneously. The test solutions were injected via a cannula in the vena cephalica antebrachii dextra. Arterial blood pressure was measured by a cannula in the femoral artery. In order to enable the registration of the myocardial contractility a Millar catheter tip pressure transducer was inserted into the left ventricle by way of the left carotid artery. Arterial blood pressure and left ventricular blood pressure were recorded continuously. Heart rate is triggered from the peak of the blood pressure signal.

From the left ventricular blood pressure the first derivative was calculated by a differentiator amplifier to give left ventricular dp/dt which was recorded as well. The compounds were solved in tetrahydrofurfurylalcohol polyethylene glycolether when necessary with additional heating.

Each dose of the test compounds was administered in a volume of 0.1 ml/kg, the duration of the injection was 1 minute.

The results with the tested compound representing the subject of invention 3,6-Dimethyl-5-[4-(1-imidazolyl)-2-thienyl]-2(1H)-pyridone-hydrochloride=A in comparison with reference substance 4,5-Dihydro-6-[4-(1-imidazolyl)-phenyl]-3(2H)-pyridazinone ((CI 914, Drugs of the Future 9 (1984), 256)=B are given in the table 1.

TABLE 1

| Compound | Dose (mg/kg) | Contractility | Heart Rate | Blood Pressure |
|---|---|---|---|---|
| B | 0.01 | +8.7 | +3.6 | −1.3 |
|   | 0.0316 | +25.5 | +18.9 | −0.7 |
|   | 0.1 | +64.8 | +15.4 | −10.4 |
| A | 0.01 | +32.4 | +5.9 | −0.2 |
|   | 0.0316 | +83.3 | +20.0 | −4.1 |
|   | 0.1 | +185.5 | +32.1 | −17.4 |

The inhibition of the collagen-induced platelets aggregation in vitro was carried out by using the method of Born (Nature, 194, 927–929 (1962)) in using a platelet rich human plasma with the substances of the present invention 3,6-dimethyl-5-[-5-(1-imidazolyl)-2-thienyl]-2(1H)-pyridone-hydrochloride=C, 3,6-dimethyl-5-[4-(1-imidazolyl)phenyl]-2(1H)-pyridone-hydrochloride=D, 5-[4-(1-imidazolyl)-2-thienyl]-6-methyl-2(1H)-pyridone-hydrochloride=E in comparison with the reference substance acetylsalicyclic acid=F.

The concentration which causes an aggregation inhibition of 50% is called IC$_{50}$ (Table 2 )

TABLE 2

| Substance | IC$_{50}$ (mole/1) |
|---|---|
| C | 4,4 × 10$^{-7}$ |
| D | 3,7 × 10$^{-7}$ |
| E | 5,4 × 10$^{-7}$ |
| F | 9,0 × 10$^{-5}$ |

The present invention also refers to pharmaceutical preparations which contain the new compounds of the formula I in form of free compounds or in form of salts thereof with pharmaceutically acceptable acids or bases. The pharmaceutical preparations according to the present invention are those for the enteric such as oral or rectal as well as parenteric administration which contain the pharmaceutically active ingredients alone or together with a common pharmaceuticall useable carrier material. Advantageously the pharmaceutical composition containing the active ingredient is present in form of single doses adapted to the desired administration such as in form of tablets, dragees, capsules, suppositories, granulate, solutions, emulsions or suspensions. The dosage of the compounds normally is in the range between 0.1 and 500 mg per day, preferably between 0.5 and 100 mg per day and it can be administered in form of a single dose or in form of several partial doses, preferably in form of two or three partial doses per day.

The preparation of the compounds of the present invention is further illustrated in the following examples. The melting points mentioned therein were determined with a Buchi-melting point determinating apparatus and are not corrected. The IR-spectra were taken by using the apparatus Nicolet NIC-3600 and the mass spectra were taken with the apparatus Varian MAT-311A (70 eV).

EXAMPLE 1

3,4-dihydro-5-[4-(1-imidazolyl)-phenyl]-6-methyl-2(1H)-pyridone

A mixture of 3 g 1-[4-(1-imidazolyl)-phenyl]-2-propanone (EPA 102 227, example 4), 30 ml 1,4-dioxane, 1,2 g acrylic acid amide and 1.73 g potassium tert-butoxide is stirred for 40 minutes at room temperature and subsequently for 2 hours at 100° C. After cooling it, water is added, the precipitated solid is sucked off, washed with water, dried and purified by column chromatography (silica gel/dichloromethan/methanol).

Yield: 1.8 g
melting point 223° C.
IR (in KBr): 1685, 1645 cm$^{-1}$.
MS [m/e]: 253 (M$^+$, 100%), 238 (17%), 224 (12%), 210 (30%), 196 (11%), 158 (12%), 157 (13%), 144 (13%), 115 (11%).

EXAMPLE 2

3,4-dihydro-3,6-dimethyl-5-[4-(1-imidazolyl)-phenyl]-2(1H)-pyridone

Similar to example 1, the reaction is carried out with 3 g 1-[4-(1-imidazolyl)-phenyl]-2-propanone, 30 ml 1,4-dioxane, 1.45 g methacrylic acid amide and 1.74 g potassium tert-butoxide.

Yield: 2.4 g.
melting point 182°-184° C.
IR (in KBr): 1678, 1643 cm$^{-1}$.
MS [m/e]: 267 (M$^+$, 100%), 252 (5%), 238 (5%), 224 (7%), 210 (44%), 196 (20%), 144 (23%), 115 (8%).

EXAMPLE 3

3,4-dihydro-4,6-dimethyl-5-[4-(1-imidazolyl)-phenyl]-2(1H)-pyridone (a)

4-[4-(1-imidazolyl)-phenyl]-3-methyl-5-oxo-hexanoic acid nitrile 1 ml of an about 5% solution of sodium ethoxide in methanol is added to a mixture of 4 g 1-[4-(1-imidazolyl)-phenyl]-2-propanone and 5 ml crotonic acid nitrile. The reaction mixture is heated for about 15 minutes to 100° C. and subsequently allowed to stand overnight at room temperature. The mixture is shaken with 20 ml of 10% acetic acid and 60 ml dichloromethane, the dichloromethan phase is dried and evaporated. The obtained oily crude product (4 g) is used in the next step without further purification.

(b)

3,4-dihydro-4,6-dimethyl-5-[4-(1-imidazolyl)-phenyl]-2(1H)-pyridone

While stirring 3.3 ml of concentrated sulfuric acid are added dropwise to a solution of 2.2 g of the crude nitrile obtained in example 3(a) in 22 ml glacial acetic acid. After stirring for 44 hours at room temperature, it is heated for 15 minutes to 100° C. After cooling, water is added, neutralized with diluted sodium hydroxide and extracted with dichloromethane. The dichloromethane phase is dried, evaporated and the residue is purified by column chromatography (silica gel/dichloromethane/methanol).

Yield: 140 mg.
melting point 188°-190° C.
IR (in KBr): 1687, 1652 cm$^{-1}$.
MS [m/e]: 267 (M$^+$, 83%), 252 (100%), 224 (12%), 128 (10%), 115 (19%).

EXAMPLE 4

3,4-dihydro-3,6-dimethyl-5-[4-(1-imidazolyl)-2-thienyl]-2(1H)-pyridone (a)

1-(2-(2-nitro-1-propenyl)-4-thienyl]-imidazole

A mixture of 94 g 4-(1-imidazolyl)-thiophene-2-aldehyde (EPA 112 987), 47.7 g nitroethane, 4.9 g β-alanine and 327 ml n-butanol is stirred for 9 hours at reflux temperature. Subsequently, it is evaporated and the residue is purified by column chromatography (silica gel//dichloromethane/methanol).

Yield: 47,7 g.
melting point 158°-159° C.
IR (in KBr): 1643, 1561, 1513, 1301 cm$^{-1}$.
MS [m/e]: 235 (M$^+$, 100%), 188 (23%), 150 (27%).

(b)

1-[4-(1-imidazolyl)-2-thienyl]-2-propanone

A mixture of 34 g (1-[2-(2-nitro-1-propenyl)-4-thienyl]-imidazole, 65 g iron powder, 0.9 ferrichloride hexahydrate, 51 ml methanol and 100 ml water are heated to reflux temperature while stirring. At this temperature, 65 ml concentrated hydrochloric acid are added dropwise within 1 hour. Subsequently, stirring is continued for 1½ hours under reflux. After cooling, the mixture is stirred into 4 times the amount of methanol. Then, it is filtrated. The filtrate is evaporated to about 1/5 of its volume and filled up with water to 500 ml. The precipitated brown deposit is sucked off, then the filtrate is extracted several times with dichloromethane. The united dichloromethane phases are dried and evaporated. The residual crude product is used in the following reaction steps without further purification.

Yield: 10g of brown oil.

(c)

3,4-dihydro-3,6-dimethyl-5-[4-(1-imidazolyl)-2-thienyl]-2(1H)-pyridone

Similar to example 1, the reaction is carried out with 2 g ketone of example 4(b), 800 mg methacrylic acid amide, 30 ml 1.4-dioxane and 1.15 g potassium tert-butoxide.

Yield: 1.6 g.
melting point 225° C.
IR (in KBr): 1678, 1636 cm$^{-1}$.
MS [m/e]: 273 (M$^+$, 100%), 258 (1%), 244 (2%), 230 (6%), 216 (9%), 202 (5%), 190 (30%), 175 (10%), 149 (3%).

EXAMPLE 5

3,4-dihydro-5-[4-(1-imidazolyl)-2-thienyl]-6-methyl-2(1H)-pyridone

Similar to example 1, the reaction is carried out with 2 g ketone of example 4(b), 810 mg acrylic acid amide, 30 ml 1,4-dioxane and 1.15 g potassium tert-butoxide.

Yield: 0.3 g.
melting point 213°–215° C. (decomposition).
IR (in KBr): 1680, 1639 cm$^{-1}$.
MS [m/e]: 259 (M+, 100%), 244 (4%), 230 (6%), 216 (10%), 190 (23%), 175 (8%).

EXAMPLE 6

3,4-dihydro-4,6-dimethyl-5-[4-(1-imidazolyl)-2-thienyl]-2(1H)-pyridone (a)

4-[4-(1-imidazolyl)-2-thienyl]-3-methyl-5-oxo-hexanoic acid nitrile

Similar to example 3(a) the reaction is carried out with 4.8 g ketone of example 4(b) and 5.8 ml crotonic acid nitrile. The oily crude product (2.3 g) is used in the next step without further purification.

(b)

3,4 dihydro-4,6-dimethyl-5-[4-(1-imidazolyl)-2-thienyl]-2(1H)-pyridone

Similar to example 3(b), the reaction is carried out with 1.8 crude nitrile from example 6(a), 18 ml acetic acid and 2.7 ml concentrated sulfuric acid.
Yield: 0.7 g.
melting point 178°–179° C.
IR (in KBr): 1681 cm$^{-1}$.
MS [m/e]: 273 (M+, 100%), 258 (76%), 230 (6%).

EXAMPLE 7

3,4-dihydro-5-[4-(2-methyl-1-imidazolyl)-phenyl]-6-methyl-2(1H)-pyridone (a) 2-methyl-1[4-(2-nitro-1-propenyl)-phenyl]-imidazole Similar to example 4(a), the reaction is carried out with 66 g 4-(2-methyl-1-imidazolyl)-benzaldehyde (DE-OS No. 33 06 196), 31.7 g nitroethane, 3.2 g β-alanine and 250 ml n-butanol.
Yield: 30 g.
melting point 164°–166° C.
IR (in KBr): 1605, 15,06, 1323 cm$^{-1}$.
MS [m/e]: 243 (M+, 100%), 196 (16%), 169 (14%), 154 (12%), 129 (21%), 128 (20%), 115 (33%).

(b)

1-[4-(2-methyl-1-imidazolyl)-phenyl]-2-propanone

Similar to example 4(b), the reaction is carried out with 30 g of the product of example 7(a), 61 g iron powder, 0.8 g ferrichloride hexahydrate, 50 ml methanol, 109 ml water and 64 ml concentrated hydrochloric acid.
Yield: 7.7 g.
melting point 96°–99° C.
IR (in KBr): 1720 cm$^{-1}$.
MS [m/e]: 214 (M+, 100%), 172 (65%), 171 (78%), 144 (46%), 90 (21%).

(c)

3,4-dihydro-5-[4-(2-methyl-1-imidazolyl)-phenyl]-6-methyl-2(1H)-pyridone

Similar to example 1, the reaction is carried out with 2 g ketone of example 7(b), 0.73 g acrylic acid amide, 1.05 potassium tert-butoxide and 30 ml 1,4-dioxane.
Yield: 0.65 g.
melting point 226°–228° C.
IR (in KBr): 1681, 1659 cm$^{-1}$.
MS [m/e]: 267 (M+, 100%), 252 (18%), 238 (12%), 224 (25%), 144 (14%).

EXAMPLE 8

3,4-dihydro-3,6-dimethyl-5-[4-(2-methyl-1-imidazolyl)-phenyl]-2(1H)-pyridone

Similar to example 1, the reaction is carried out with 7.6 g ketone from example 7b), 3,3 g methacrylic acid amide, 4 g potassium tert-butoxide and 80 ml 1,4-dioxane.
Yield: 5.2 g.
melting point 202°–204° C.
IR (in KBr): 1681, 1650 cm$^{-1}$.
MS [m/e]: 281 (M+, 100%), 266 (6%), 224 (31%), 210 (16%), 144 (26%).

EXAMPLE 9

3,4-dihydro-3,6-dimethyl-5-[5-(1-imidazolyl)-2-thienyl]-2(1H)-pyridone (a)

1-[5-(2-nitro-1-propenyl)-2-thienyl]-imidazole

Similar to example 4(a), the reaction is carried out with 60 g 5-(1-imidazolyl)-thiophene-2-aldehyde (EPA No. 112 987), 23.1 g nitroethane, 2 4 g β-alanine and 210 ml n-butanol.
Yield: 40.7 g.
melting point 145°–147° C.
IR (in KBr): 1631, 1543, 1512, 1304 cm$^{-1}$.
MS [m/e]: 235 (M+, 27%), 178 (100%), 168 (16%), 150 (29%), 123 (21%).

(b)

1-[5-(1-imidazolyl)-2-thienyl]-2-propanone

Similar to example 4(b), the reaction is carried out with 35 g of the product of example 9(a), 73.6 g iron powder, 1 g ferrichloride hexahydrate, 60 ml methanol, 125 ml water and 75 ml concentrated hydrochloric acid.
Yield: 10.7 oil.
IR (in substance): 1713 cm$^{-1}$.
MS [m/e]: 206 (M+, 27%), 164 (21%), 163 (100%), 136 (16%), 109 (20%).

(c)

3,4-dihydro-3,6-dimethyl-5-[5-(1-imidazolyl)-2-thienyl]-2(1H)-pyridone

Similar to example 1, the reaction is carried out with 10.7 g ketone of example 9(b), 4.8 methacrylic acid amide, 5.8 g potassium tert-butoxide and 100 ml 1,4-dioxane.
Yield: 6.3 g.
melting point 136° C.
IR (in KBr): 1671, 1634 cm$^{-1}$.
MS [m/e]: 273 (M+, 100%), 258 (1%), 230 (8%), 150 (23%), 149 (23%).

EXAMPLE 10

1,2-dihydro-5-[4-(1-imidazolyl)-2-thienyl]-6-methyl-2-oxo-pyridine-3-carboxylic acid nitrile A mixture of 7 g ketone from example 4b), 70 ml N,N-dimethylformamide dimethylacetal and 120 ml acetonitrile is stirred for 18 hours at room temperature. Then it is evaporated. To the residue are added 140 ml dimethylformamide, 7 g cyanoacetamide and 8.4 g sodium methoxide and the resulting mixture is refluxed for 1½ hours. Then it is evaporated, to the residue are added 120 ml methanol and 40 ml glacial acetic acid and it is stirred for 20 minutes at room temperature. The precipitated solid is sucked off and then purified by column chromatography (silica gel//dichloromethane/methanol).
Yield: 3.5 g.
melting point 300° C. (decomposition).
IR (in KBr): 2225, 1679 cm$^{-1}$.
MS [m/e]: 282 (M+, 100%), 254 (4%), 228 (5%).

EXAMPLE 11

1,2-dihydro-5-[5-(1-imidazolyl)-2-thienyl]-6-methyl-2-oxo-pyridine-3-carboxylic acid nitrile Similar to example 10, the reaction is carried out with 2.3 g ketone of example 9(b), 2.3 ml N,N-dimethylformamide dimethylacetal, 20 ml acetonitrile, 40 ml dimethylformamide, 2.1 g cyanoacetamide and 2.7 g sodium methoxide.
Yield: 0.96 g.
melting point 277°-280° C.
IR (in KBr): 2223, 1672 cm$^{-1}$.
MS [m/e]: 282 (M+, 100%), 267 (3%), 249 (9%), 228 (14%).

EXAMPLE 12

1,2-dihydro-5-[4-(1-imidazolyl)-2-thienyl]-6-methyl-2-oxo-pyridine-3-carboxylic acid 3.5 g nitrile of example 10 are stirred at reflux temperature for 5 hours in 50 ml concentrated hydrochloric acid. After cooling, it is neutralized with sodium hydroxide, the precipitated solid is sucked off, washed with water and recristallized from dimethylformamide/water using activated charcoal.
Yield: 2.4 g.
melting point 298°-300° C. (decomposition).
IR (in KBr): 1737, 1641 cm$^{-1}$.
MS [m/e]: 301 (M+, 30%), 257 (100%), 229 (12%).

EXAMPLE 13

1,2-dihydro-5-[5-(1-imidazolyl)-2-thienyl]-6-methyl-2-oxo-pyridine-3-carboxylic acid Similar to example 12, the reaction is carried out with 0.66 g nitrile of example 11 and 20 ml concentrated hydrochloric acid.
Yield: 0.58 g.
melting point 278° C. (decomposition).
IR (in KBr): 1732, 1639 cm$^{-1}$.
MS [m/e]:301 (M+, 100%), 283 (37%), 257 (35%), 242 (4%), 216 (13%).

EXAMPLE 14

5-[4-(1-imidazolyl)-2-thienyl]-6-methyl-2-(1H)-pyridone 1 g of the acid of example 12 is stirred at reflux temperature for 2 hours in 30 ml diphenylether. After cooling, the mixture is partitioned between dichloromethane and 7% hydrochloric acid. The aqueous phase is washed several times with dichloromethane and then brought to pH 7 by addition of sodium hydroxide. The precipitated solid is sucked off, washed with water and dried. For its purification, it is dissolved in a mixture of dichloromethane and methanol. After the addition of activated charcoal, it is boiled for a short time and the mixture is filtrated through a silica gel layer. The solid precipitated during evaporation of the filtrate is sucked off and dried.
Yield: 280 mg.
melting point 230° C.
IR (in KBr): 1659 cm$^{-1}$.
MS [m/e]: 257 (M+, 100%), 242 (3%), 229 (12%), 203 (4%), 187 (5%).

EXAMPLE 15

5-[5-(1-imidazolyl)-2-thienyl]-6-methyl-2(1H)-pyridone

Similar to example 14, the reaction is carried out with 0.57 g of the acid of example 13 and 20 ml diphenyether.
Yield: 0.18 g.
melting point 233° C.
IR (in KBr): 1656 cm$^{-1}$.
MS [m/e]: 257 (M+, 100%), 242 (2%), 229 (4%), 203 (4%), 187 (5%).

EXAMPLE 16

3,6-dimethyl-5-[4-(1-imidazolyl)-phenyl]-2(1H)-pyridone

A solution of 0.31 ml bromine in 3.1 ml glacial acetic acid is added dropwise within 20 minutes to a solution of 1.2 g dihydropyridone obtained in example 2 in 26 ml glacial acetic acid at 100° C. Subsequently, it is stirred for 5 hours at this temperature. After cooling, the precipitated solid is sucked off and suspended in water. The obtained mixture is brought to pH 7 by the addition of sodium hydroxide and stirred over-night at room temperature. Then, it is sucked off, the solid is dried and purified by column chromatography (silical gel//dichloromethane/methanol).
Yield: 0.2 g.
melting point >300° C. (decomposition).
IR (in KBr): 1642 cm$^{-1}$.
MS [m/e]: 265 (M+, 100%), 250 (2%), 236 (19%), 195 (6%), 168 (6%), 154 (5%), 128 (6%).

EXAMPLE 17

3,6-dimethyl-5-[4-(1-imidazolyl)-2-thienyl/-2(1H)-pyridone

A mixture of 1.08 g 3,4-dihydropyridone from example 4(c), 1.14 g 3-nitrobenzene sulfonic acid sodium salt, 0.8 g sodium hydroxide and 25 ml water are stirred for 20 hours at the reflux temperature. After cooling, it is neutralized with acetic acid, the precipitated solid is sucked off, dried and purified by column chromatography (silica gel//dichloromethane/methanol).
Yield: 0.25 g.
melting point 250° C. (decomposition).
IR (in KBr): 1658 cm$^{-1}$.
MS [m/e]:271 (M+, 100%), 256 (5%), 243 (11%), 242 (12%), 201 (6%), 174 (4%), 160 (4%), 135 (5%), 108 (6%).

EXAMPLE 18

3,6-dimethyl-5-[4-(1-imidazolyl)-2-thienyl]-2(1H)-pyridone

A mixture of 2.5 g 3,4-dihydropyridone from example 4(c), 0.5 g sulfur powder and 50 ml of an eutectic mixture of diphenyl and diphenylether (Dowtherm A) is heated to 190°-200° C. for 2 hours. After cooling to room temperature, it is shaken with ether/diluted hydrochloric acid, the hydrochloric acid phase is neutralized with an ammonium hydroxide solution, the precipitated solid is sucked off, dried and purified by column chromatography (silica gel//dichloromethan/methanol).

Yield: 1 g.

melting point 252° C. (decomposition).

EXAMPLE 19

3,6-dimethyl-5[5-(1-imidazolyl)-2-thienyl]-2(1H)-pyridone

Similar to example 18, the reaction is carried out with 4 g 3,4-dihydropyridone from example 9(c), 0.8 g sulfur powder and 80 ml of the eutectic mixture of diphenyl and diphenylether.

Yield: 0.7 g.

melting point 202°-204° C. (decomposition).

IR (in KBr): 1645 cm$^{-1}$.

MS [m/e]: 271 (M+, 100%), 256 (1%), 243 (2%), 242 (3%), 201 (3%), 174 (2%), 160 (2%), 135 (2%).

EXAMPLE 20

3,6-dimethyl-5-[4-(2-methyl-1-imidazolyl)-phenyl]-2(1H)-pyridone

A mixture of 5.2 g dihydropyridone from example 8, 0.6 g sulfur powder and 13 ml of the eutectic mixture of diphenyl and diphenylether is stirred for 2 hours at 195° to 200° C. After cooling to room temperature, it is extracted with 70 ml diluted hydrochloric acid. The aqueous phase is treated twice at 50° C. with activated charcoal, then it is evaporated to 15 ml and neutralized with a diluted ammonium hydroxide solution. The precipitated solid is sucked off, dried and purified by column chromatography (silica gel//dichloromethan/methanol).

Yield: 1.9 g.

melting point 291° C. (decomposition).

IR (in KBr): 1643 cm$^{-1}$.

MS [m/e]: 279 (M+, 100%), 265 (4%), 252 (5%), 251 (6%), 209 (4%), 196 (4%), 168 (5%), 154 (5%), 140 (6%), 128 (6%), 105 (5%).

EXAMPLE 21

4,6-dimethyl-5-[4-(1-imidazolyl)-2-thienyl]-2(1H)-pyridone 2 g ketone from example 4b) are dissolved in 5 ml methane sulfonic acid. 0.68 g aceto acetic acid amide and 5.4 g polyphosphoric acid are added and the mixture is heated for 90 minutes to 120°-130° C. After cooling, the reacted mixture is stirred into ice water and neutralized with an ammonium hydroxide solution. Then it is extracted with dichloromethane, the dichloromethan phase is dried, evaporated and the residue is purified by column chromatography (silica gel//dichloromethan/methanol).

Yield: 0.3 g.

melting point 243° C. (decomposition).

IR (in KBr): 1656 cm$^{-1}$.

MS [m/e]: 271 (M+, 100%), 256 (1%), 243 (16%), 228 (3%), 201 (4%), 136 (4%).

EXAMPLE 22

3,4-dihydro-5-[4-(1-imidazolyl)-phenyl]-6-methyl-2(1H)-pyridone-hydrochloride 50 ml of ethanolic hydrochloric acid are added to a mixture of 0.7 g 3,4-dihydro-5-[4-(1-imidazolyl)-phenyl]-6-methyl-2(1H)-pyridone and 20 ml ethanol. After stirring for 30 minutes, it is filled up with ether to 300 ml and stirred for further 20 minutes. After sucking off and drying, the water soluble hydrochloride is obtained having a melting point of 304° C. (decomposition).

Similar to example 22, the following compounds are prepared:

3,4-dihydro-3,6-dimethyl-5-[4-(1-imidazolyl)-phenyl]-2(1H)-pyridone-hydrochloride, melting point 285°-287° C. (decompos.)

3,4-dihydro-4,6-dimethyl-5-[4-(1-imidazolyl)-phenyl]-2(1H)-pyridone-hydrochloride, melting point 284° C. (decomp.)

3,4-dihydro-3,6-dimethyl-5-[4-(1-imidazolyl)-2-thienyl]-2(1H)-pyridone-hydrochloride, melting point 245°-248° C. (decomp.)

1,2-dihydro-5-[4-(1-imidazolyl)-2-thienyl]-6-methyl-2-oxo-pyridin-3-carboxylic acid nitrile hydrochloride, melting point 318° C. (decomposition)

1,2-dihydro-5-[4-(1-imidazolyl)-2-thienyl]-6-methyl-2-oxo-pyridin-3-carboxylic acid hydrochloride, melting point 294°-296° C. (decomposition)

5-[4-(1-imidazolyl)-2-thienyl]-6-methyl-2(1H)-pyridone hydrochloride, melting point 287°-289° C. (decomposition)

3,6-dimethyl-5-[4-(1-imidazolyl)-phenyl]-2(1H)-pyridone hydrochloride, melting point >300° C. (decomposition)

3,6-dimethyl-5-[4-(1-imidazolyl)-2-thienyl]-2(1H)-pyridone hydrochloride, melting point 306° C. (decomposition)

3,4-dihydro-4,6-dimethyl-5-[4-(1-imidazolyl)-2-thienyl]-2(1H)-pyridone-hydrochloride, melting point 140° C. (decomp.)

3,4-dihydro-5-[4-(2-methyl-1-imidazolyl)-phenyl]-6-methyl-2(1H)-pyridone-hydrochloride, melting point 312°-315° C. (decomp)

3,4-dihydro-3,6-dimethyl-5-[4-(2-methyl-1-imidazolyl)-phenyl]-2(1H)-pyridone-hydrochloride, melting point 315° C. (decomposition)

3,4-dihydro-3,6-dimethyl-5-[5-(1-imidazolyl)-2-thienyl]-2(1H)-pyridone-hydrochloride, melting point 273° C. (decomp.)

1,2-dihydro-5-[5-(1-imidazolyl)-2-thienyl]-6-methyl-2-oxo-pyridin-3-carboxylic acid nitrile hydrochloride, melting point 310° C. (decomposition)

5-[5-(1-imidazolyl)-2-thienyl]-6-methyl-2(1H)-pyridone hydrochloride, melting point 287° C. (decomposition)

3,6-dimethyl-5-[5-(1-imidazolyl)-2-thienyl]-2(1H)-pyridone hydrochloride, melting point 298° C. (decomposition)

3,6-dimethyl-5-[4-(2-methyl-1-imidazolyl)-phenyl]-2(1H)-pyridone-hydrochloride, melting point 310° C. (decomposition)

4,6-dimethyl-5-[4-(1-imidazolyl)-2-thienyl]-2(1H)-pyridone hydrochloride, melting point 310° C. (decomposition).

What we claim is:

1. 2(1H)-Pyridones of formula I

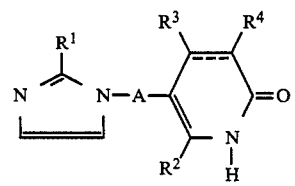

wherein

==== is a single bond between two carbon atoms, $R^1$, $R^3$ and $R^4$ each represent a member selected from the group consisting of hydrogen and methyl, $R^2$ is a $C_{1-4}$-lower alkyl group and A is a member selected from the thienylene groups.

2. 2(1H)-Pyridones of formula I according to claim 1 wherein A is a member selected from the group consisting of the 2,4-thienylene and 2,5-thienylene groups.

3. 2(1H)-Pyridones of formula I

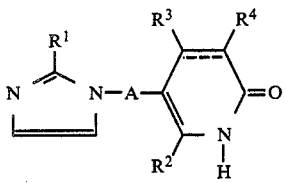

wherein

==== is a double bond between two carbon atoms.

$R^1$ and $R^3$ each represent a member selected from the group consisting of hydrogen and methyl, $R^2$ is a $C_{1-4}$-lower alkyl group, $R^4$ is a member selected from the group consisting of hydrogen and methyl, A is a member selected from the group consisting of 2,4-thienylene of the formula

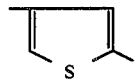

and 2,5-thienylene of the formula

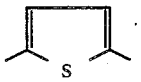

4. 3,6-Dimethyl-5-[4-(1-imidazolyl)-2-thienyl]-2(1H)-pyridone or a pharmacologically acceptable acid addition salt thereof.

5. 3,6-Dimethyl-5-[5-(1-imidazolyl)-2-thienyl]-2(1H)-pyridone or a pharmacologically acceptable acid addition salt thereof.

6. 5-[4-(1-Imidazolyl)-2-thienyl]-6-methyl-2(1H)-pyridone or a pharmacologically acceptable acid addition salt thereof.

7. A method for the treatment of human beings suffering from congestive heart failure comprising administering to such human beings a compound according to claim 1 in a daily dose between 0.1 and 500 mg.

8. A method for the treatment of human beings suffering from congestive heart failure comprising administering to such human beings a compound according to claim 5 in a daily dose between 0.1 and 500 mg.

* * * * *